(12) United States Patent
Probe et al.

(10) Patent No.: US 9,320,555 B2
(45) Date of Patent: Apr. 26, 2016

(54) MODULAR LAG SCREW

(71) Applicant: Stryker Trauma GmbH, Schönkirchen (DE)

(72) Inventors: Robert Probe, Temple, TX (US); Martje Paulsen, Kiel (DE); Bernd Simon, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 321 days.

(21) Appl. No.: 13/755,677

(22) Filed: Jan. 31, 2013

(65) Prior Publication Data

US 2014/0214098 A1 Jul. 31, 2014

(51) Int. Cl.
*A61B 17/04* (2006.01)
*A61B 17/86* (2006.01)
*A61F 2/08* (2006.01)
*A61B 17/74* (2006.01)

(52) U.S. Cl.
CPC ............ *A61B 17/8685* (2013.01); *A61B 17/744* (2013.01); *A61B 17/8605* (2013.01)

(58) Field of Classification Search
CPC ............. A61B 17/864; A61B 17/8685; A61B 17/8605; A61B 17/68; A61B 17/744
See application file for complete search history.

(56) References Cited

U.S. PATENT DOCUMENTS

| | | | |
|---|---|---|---|
| 4,432,358 A | 2/1984 | Fixel | |
| RE33,348 E | 9/1990 | Lower | |
| 5,620,445 A | 4/1997 | Brosnahan et al. | |
| 5,653,709 A | 8/1997 | Frigg | |
| 5,855,579 A | 1/1999 | James et al. | |
| 5,971,986 A | 10/1999 | Santori et al. | |
| 6,423,066 B1 | 7/2002 | Harder et al. | |
| 6,443,954 B1 | 9/2002 | Bramlet et al. | |
| 6,488,684 B2 | 12/2002 | Sterghos et al. | |
| 6,648,889 B2 | 11/2003 | Bramlet et al. | |
| 7,972,336 B2 | 7/2011 | James et al. | |

(Continued)

FOREIGN PATENT DOCUMENTS

| | | |
|---|---|---|
| CN | 102119870 A | 7/2011 |
| EP | 1175872 A2 | 1/2002 |

(Continued)

OTHER PUBLICATIONS

Lasanianos et al., "Hip screw lateral migration with no cut-out or non-union implication: a case report", Case Journal 2:6419, 2009.

(Continued)

*Primary Examiner* — Christopher Beccia
*Assistant Examiner* — Diana S Jones
(74) *Attorney, Agent, or Firm* — Lerner, David, Littenberg, Krumholz & Mentlik, LLP

(57) ABSTRACT

An elongated modular implant is provided which has a distal part and a proximal part both having a leading end and a trailing end, respectively. The trailing end of the distal part includes a tool engagement portion and the leading end of the proximal part includes a distal part engagement portion for an engagement with the tool engagement portion of the distal part. The implant further includes an assembly element for firmly coupling the distal part and the proximal part when the first tool engagement portion of the distal part engages the distal part engagement portion of the proximal part. The proximal part trailing end may also have a tool engagement portion identical to the trailing end of the distal part.

19 Claims, 7 Drawing Sheets

(56) References Cited

U.S. PATENT DOCUMENTS

| | | |
|---|---|---|
| 2007/0270847 A1 | 11/2007 | Shaw |
| 2008/0177334 A1 | 7/2008 | Stinnette |
| 2008/0281326 A1 | 11/2008 | Watanabe et al. |
| 2011/0066152 A1 | 3/2011 | Keller et al. |
| 2011/0190830 A1* | 8/2011 | Biedermann et al. ......... 606/305 |
| 2012/0253346 A1 | 10/2012 | Lee et al. |

FOREIGN PATENT DOCUMENTS

| | | |
|---|---|---|
| EP | 2343020 A1 | 7/2011 |
| JP | 2005511238 A | 4/2005 |
| JP | 2009207710 A | 9/2009 |
| WO | 03051210 A2 | 6/2003 |

OTHER PUBLICATIONS

Li et al., "Medial pelvic migration of the lag screw in a short gamma nail after hip fracture fixation: a case report and review of the literature", Journal of Orthopaedic Surgery and Research 5:62, 2010.
European Examination Report for Application No. 13153466.1 dated May 7, 2015.
Chinese Office Action and Search Report for Application No. 201410044881.7 dated Sep. 1, 2015.

* cited by examiner

MODULAR LAG SCREW

BACKGROUND OF THE INVENTION

The invention relates to an implant. In particular, the invention relates to a bone screw like a lag screw to be received in a transverse through bore in a bone nail or hip plate.

An implant and particularly a bone implant include a portion or section or end which is adapted to be firstly introduced into a body during an implantation. In the description below, such a portion or section or end is referred to as leading portion or leading section or leading end. Consequently, an opposite portion or section or end of the implant is adapted to be introduced last, wherein this portion or section or end may additionally be configured for an engagement of a tool for inserting the implant into the body. Below, such a portion or section or end is referred to as trailing portion or trailing section or trailing end.

A bone implant may be a pin or a nail or screw or plate. A bone nail may be an intramedullary nail, for example a femur nail, a humerus nail or a tibia nail. A bone screw may be a screw for fixing fragments of a bone fracture or may be a locking screw for locking a bone nail in the bone.

However, due to the anatomical variation of bones it may happen that the trailing end of a bone implant extends out of a bone after implant placement. The trailing end of the implant may act as an interface with an implantation tool and may thus be provided with an appropriate structure like, for example, slots for controlling the forces applied during implant insertion and removal. It may occur that patients complain about pain after surgery in this area, especially when the implant is extending out of the bone. This pain may be caused by sharp edges at the trailing end of the implant. Such edges may cause irritation and/or injury to the surrounding soft tissue.

A migration of a hip screw is reported in the case report "Hip screw lateral migration with no cut-out or non-union implication: a case report" of Nikolaos Lasanianos et al. (Case Journal 2009, 2:6419). A similar report can be found in "Medial pelvic migration of the lag screw in a short gamma nail after hip fracture fixation: a case report and review of the literature" of Xinning Li et al. (Journal of Orthopaedic Surgery and Research 2010, 5:62).

BRIEF SUMMARY OF THE INVENTION

One aspect of the invention may be defined as providing an implant causing less irritation of surrounding tissue when being implanted.

This is achieved by the bone screw according to the independent claim. Further embodiments are described in the dependent claims.

In general, an elongated implant like a bone screw according to one embodiment is a modular screw which has a distal part having a leading end and a trailing end, designated herein as a first leading end and a first trailing end. The first trailing end includes a tool engagement portion designated herein as first tool engagement portion. The modular implant further has a proximal part also having a leading end and a trailing end. The ends of the proximal part are designated herein as a second leading end and a second trailing end, respectively, wherein the second leading end includes an engagement portion for an engagement with the tool engagement portion of the first trailing end of the distal implant part, therefore designated as distal part engagement portion, and wherein the second trailing end also includes a tool engagement portion wherein this one is designated as second tool engagement portion. The implant further includes an assembly element, such as a screw, for firmly coupling the distal part and the proximal part when the first tool engagement portion of the distal part engages the distal part engagement portion of the proximal part.

In other words, the implant comprises two parts which can be assembled so as to form a single implant, wherein the distal part is adapted to be introduced into a body first and the proximal part is adapted to follow the distal part during an implantation and thus to be introduced into the body last. It is noted that the distal part may be used as an implant without the proximal part.

Such a combination of parts as an implant allows the surgeon to shorten the implant once protrusion of the implant out of for example a bone has occurred due to bone fragment compression. Such a shortening may be accomplished in a short procedure leaving at least the distal part of the implant in place which may be crucial as the probability of removal, patient outcome and stability are influenced by the implant. Accordingly, an implant is provided which can be assembled pre-operatively with a distal part and a proximal part, either at the time of manufacture or in the operating room, and can be disassembled by a smaller surgery merely removing the proximal part.

According to an embodiment, the first tool engagement portion of the distal part includes at least one slot and the distal part engagement portion of the proximal part comprises at least one protrusion for an engagement with the at least one slot so that particularly rotational forces can be transmitted from the proximal part to the distal part. It will be understood that the protrusion may have any suitable shape, for example a shape of a circular or rectangular pin, of a prong, spike or tooth.

According to one embodiment, the first tool engagement portion of the distal part is crown-shaped. It is noted that the distal part engagement portion may have any shape which is suitable to transmit forces, in particular rotational forces from the proximal part to the distal part.

According to one embodiment, the distal part engagement portion of the proximal part is formed so as to provide a form-fit with the tool engagement portion of the distal part. It can be seen as an advantage of a form-fit connection that no gaps or free edges may exist between the distal and proximal parts.

According to a further embodiment, the trailing end of the proximal part may be provided with a tool engagement portion corresponding to the tool engagement portion of the trailing end of the distal part. Accordingly, the distal part engagement portion at the leading end of the proximal part may be formed for an engagement with the tool engagement portion at the trailing end of the distal part, and the trailing end of the proximal part may comprise a second tool engagement portion which corresponds to the first tool engagement portion.

Such a proximal part can be understood as an extension of the distal part as a tool which fits to the first tool engagement portion of the distal part may also fit into the second tool engagement portion of the proximal part. It will be understood that it may be possible to further extend the length of the implant by an additional proximal part when coupling the leading end of the additional proximal part to the trailing end of another proximal part. Of course proximal parts of different lengths can be provided.

According to one embodiment, the implant is a bone implant, in particular a bone screw and the proximal part comprises an end surface which corresponds to a shape of an outer bone surface at an intended implantation site and is smooth so that the end surface of the implant can be flush with the bone surface surrounding the end surface when the implant is inserted into the bone. For example, the end surface may be curved in one direction to fit to the shape of an outer surface of a more or less circular long bone when implanted substantially perpendicular to the bone axis, like for example a locking screw of an intramedullary nail, or the end surface may be shaped as a saddle to match the outer surface at a greater trochanter of a femur. Alternatively, the end surface may be inclined with respect to a longitudinal axis of the implant when the implant, for example a lag screw, is introduced into a bone with an angle relative to the outer surface of the bone.

It will be understood that "smooth" refers to a shape without any edges, in particular without any sharp edge. That is, the end surface may be formed without any discontinuities. The edge between the end surface and an circumferential outer surface of the implant may be provided with a chamfer or may be rounded so as to be also smooth, i.e. so as to not form any edge at which irritation of soft tissue may occur when the tissue is in contact with a trailing section of the implant including the end surface.

According to another embodiment, the distal part comprises an axial bore with an inner thread at the first trailing end, and the proximal part comprises an axial through bore with an enlarged section, and the assembly screw comprises a screw head being adapted to be received in the enlarged section in the proximal part and an outer screw thread being adapted to engage the inner thread in the distal part so as to firmly couple the distal part and the proximal part.

According to one embodiment, the distal part and the proximal part are configured to move over a guide wire when the implant is assembled, i.e. when the first tool engagement portion of the distal part engages the distal part engagement portion of the proximal part. Accordingly, the implant may further comprise a cannulation or through bore extending in a longitudinal direction of the shaft, for accommodating a guide wire.

It has to be noted that a person skilled in the art will gather from the above and the following description that, unless otherwise notified, in addition to any combination of features belonging to one embodiment, also any combination of features relating to another embodiment is considered to be disclosed with this application.

These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of exemplary embodiments with reference to the attached drawings.

DETAILED DESCRIPTION

Figure 1A:
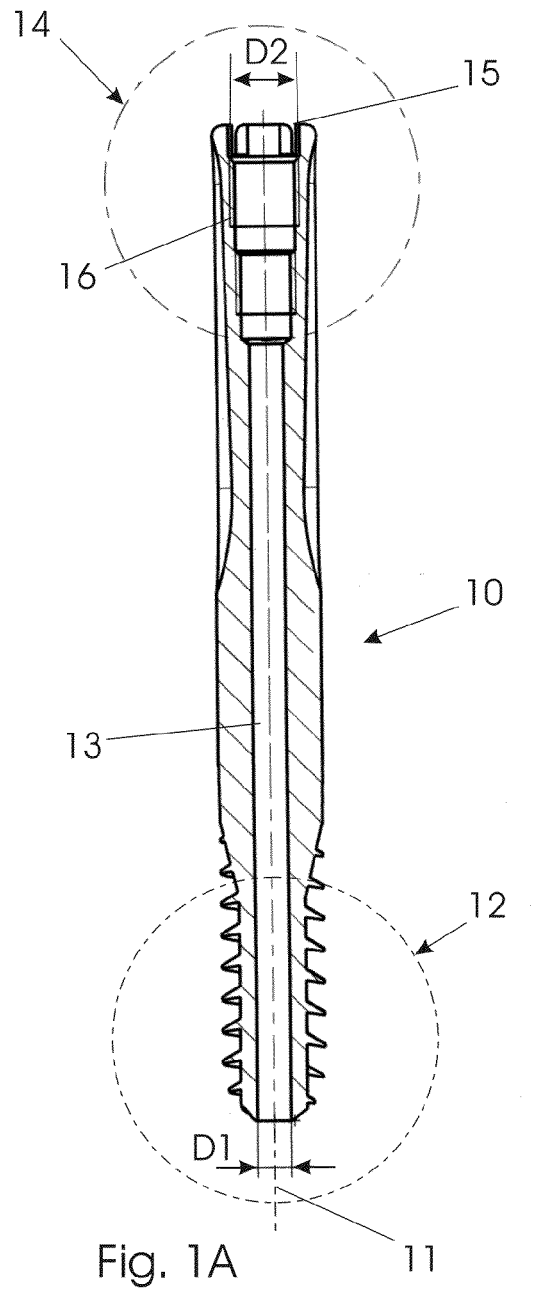
FIG. 1A is a sectional view.

Embodiments of an implant are shown in the FIGS. and described below, comprising a bone screw as a distal part, two different proximal parts as bone screw extensions as well as two different assembly screws for coupling at least one of the proximal parts with the distal part.

In general, the distal part 10 as well as the assembly element 30 comprises an axial through bore 13 having a diameter D1, for accommodating a guide wire. At the trailing section of the distal part 10, a threaded bore 16 with an outer diameter D2 is provided, for receiving outer threads of an assembly element 30 having a corresponding diameter D2' (FIG. 4B). The proximal part 20 also includes a bore section with a diameter D2 allowing an assembly element 30 to extend through that bore section of the proximal part 20. Furthermore, the proximal part 20 includes an enlarged bore section having a diameter D3 for accommodating a head 31 of the assembly element 30 having an outer diameter D3' which is slightly smaller than the diameter D3 in the enlarged bore section of the proximal part to easily fit into that bore section. Referred to as D4 is an outer diameter of an inner thread in the proximal part 20 for accommodating a threaded screw head 31 with a diameter D4' which should also be slightly smaller to easily fit into that inner thread. Finally, an outer diameter D5 denotes an overall outer diameter of the implant, that is, of the distal part as well as of any of the proximal parts.

Figure 1B:
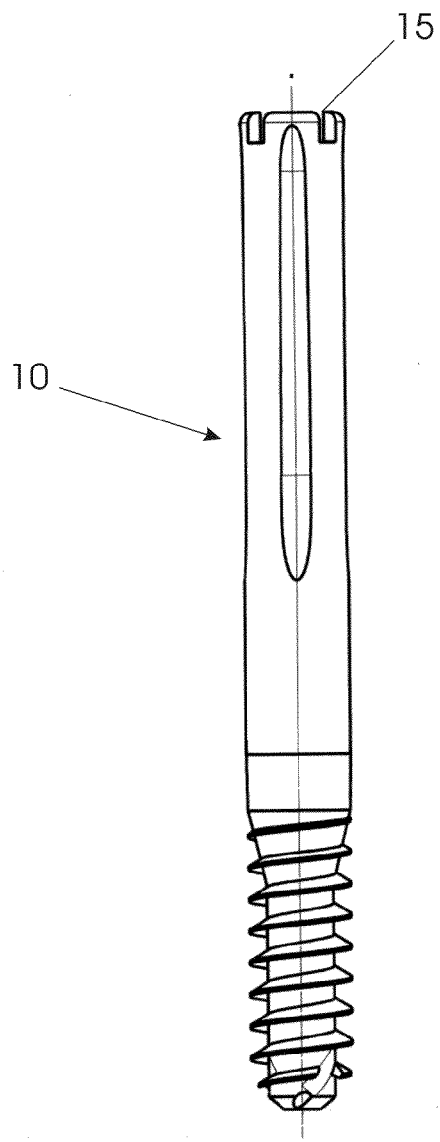
FIG. 1B is a side view and FIG. 1C is a top view of a distal part of a bone screw.
Figure 1C:
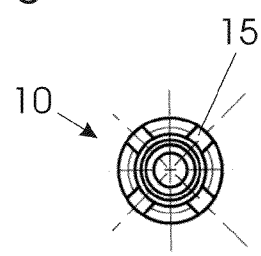

As shown in FIGS. 1A, 1B and 1C, a distal part 10 may comprise a longitudinal axis 11, a leading end section 12, an axial through bore 13, a trailing end section 14, a tool engagement portion 15 as well as a threaded bore 16. At the leading end section 12, an outer thread is provided so that the implant can be screwed in into a bone. The axial through bore 13 is a central through bore for accommodating a guide wire. In the trailing end section 14, the axial bore has an enlarged portion in which an inner thread is provided. The threaded bore 16 is provided for receiving an assembly element in case a proximal part 20 is to be coupled to the trailing end of the distal part 10. The tool engagement portion 15 can be described as crown-shaped having four slots which extend in a longitudinal direction of the distal part 10 and which are evenly, i.e. every degrees, arranged on the circumference at the trailing end section 14 of the distal part 10.

Figure 2A:
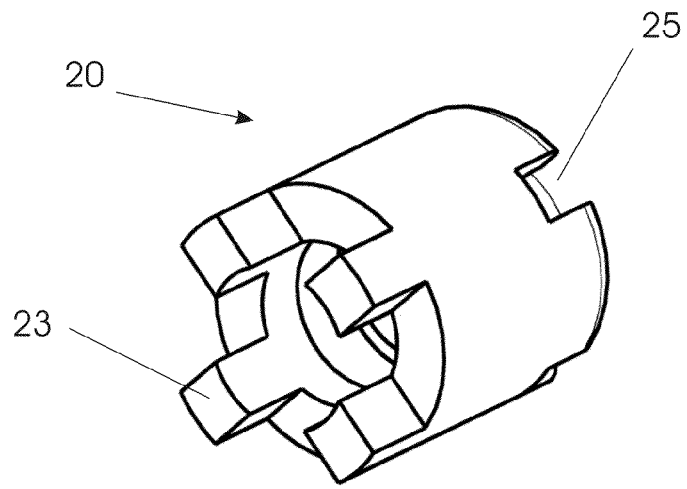
FIG. 2A is an isometric view and FIG. 2B is a sectional view of a proximal part according to a first embodiment.
Figure 2B:
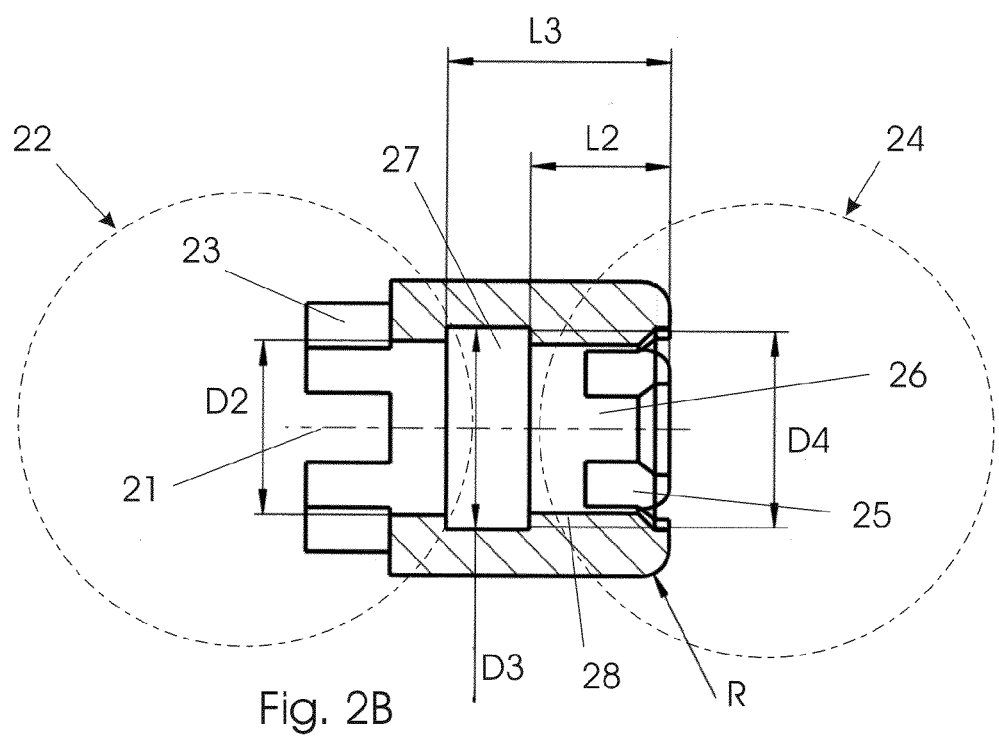

FIGS. 2A and 2B show a first embodiment of a proximal part 20. The proximal part 20 comprises a leading end section 22 as well as a training end section 24. The leading end section 22 comprises four protrusions 23 which are configured to fit into the slots of the tool engagement portion 15 at the trailing end section 14 of the distal part 10. At the opposite end, i.e. at the trailing end section 24, slots 25 are provided forming a tool engagement portion which corresponds to the tool engagement portion 15 of the distal part 10. Furthermore, the proximal part comprises a through bore 26 extending along a longitudinal axis 21, wherein the through bore 26 includes an enlarged section 27. By the enlarged section 27, a shoulder is formed on which a head of an assembly element 30 may abut so that the proximal part 20 may be firmly coupled to the distal part 10 when an assembly element 30 is inserted into the proximal part with the head abutting at the shoulder formed by the enlarged section 27 and with a threaded portion extending into the distal part and in particular into the threaded bore 16 of the distal part 10.

Figure 3A:
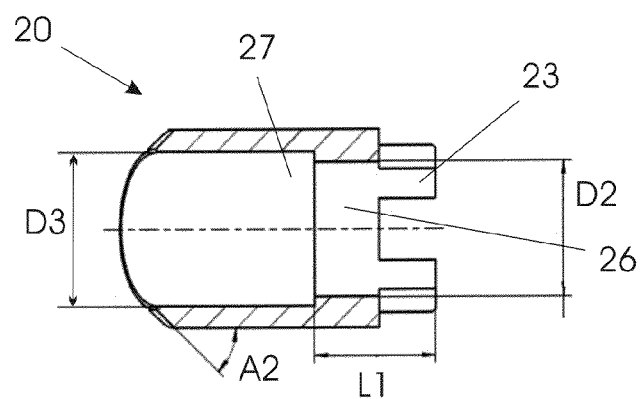
FIG. 3A is a sectional view and FIG. 3B is a side view of a proximal part according to a second embodiment.
Figure 3B:
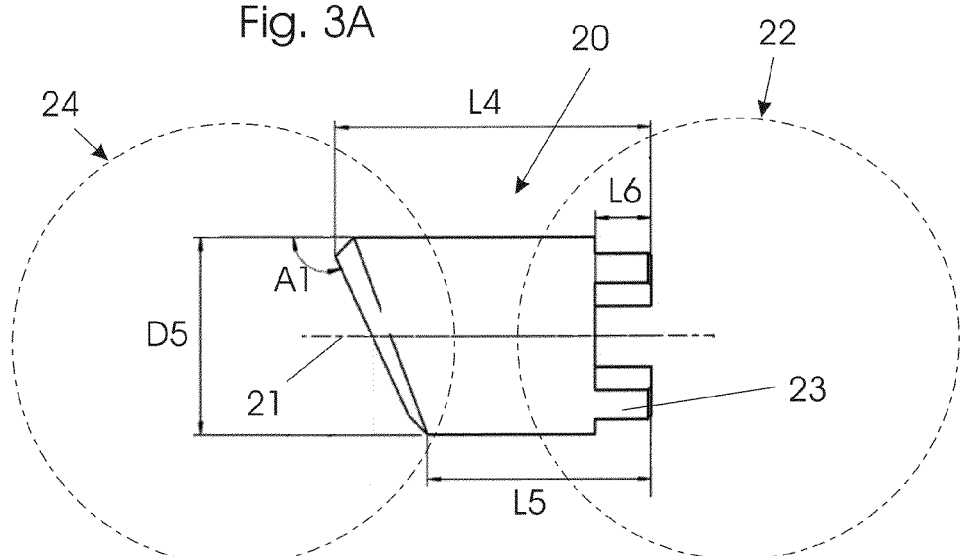

FIGS. 3A and 3B show a second embodiment of a proximal part 20. The proximal part 20 comprises a leading end section 22 and a trailing end section 24 wherein the leading end section 22 is formed comparable with the leading end section 22 of the first embodiment of a proximal part as shown in FIGS. 2A and 2B. At the trailing end section 24, an inclined end surface is formed, with an inclination angle A1. An implant with a proximal part 22 having an inclined end surface and a distal part 10 can be introduced into a bone with an angle A1 relative to the outer bone surface so that the end surface of the proximal part being arranged so as to form a flush surface with the surrounding outer bone surface when the implant is implanted. Furthermore, the outer edge of the end surface may have a chamfer with an angle A2 relative to the outer circumferential surface of the proximal part.

Figure 4A:
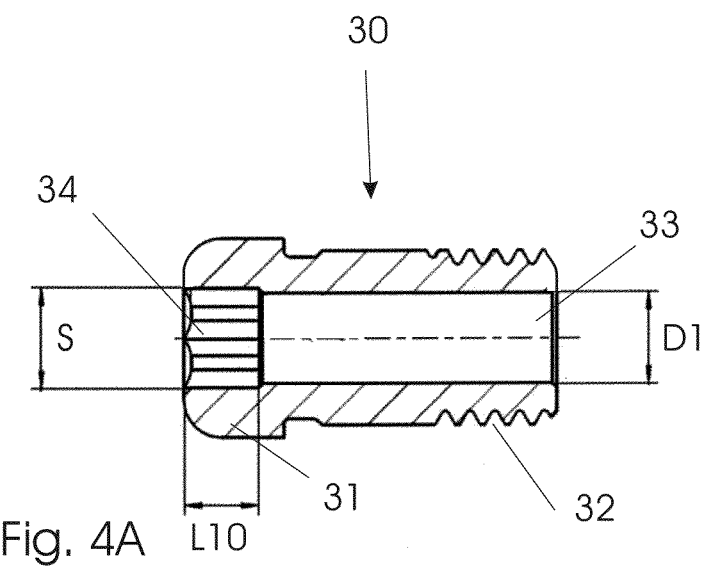
FIG. 4A is a sectional view and FIG. 4B is a side view of an assembly element according to a first embodiment.
Figure 4B:
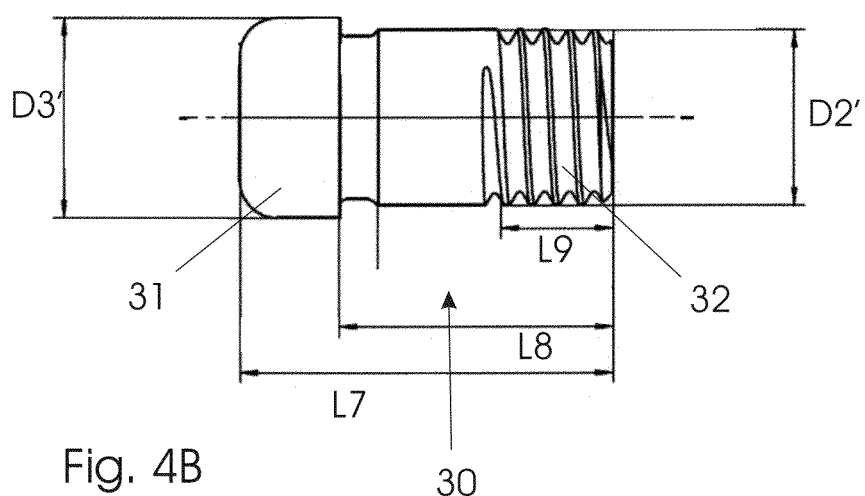

FIGS. 4A and 4B show a first embodiment of an assembly element 30 which is in this example an assembly screw 30. The assembly screw 30 comprises an outer thread 32 as well as a head 31. Furthermore the assembly screw 30 is cannulated, i.e. comprises an axial through bore 33. In the head 31 of the assembly screw 30, an inner tool engagement portion is provided, for example for a screwdriver. It will be understood, that the width across flats S is preferably greater than the diameter D1 of the through bore 33. The outer diameter D2' should be configured to fit with a loose fit to the diameter D2 of the inner thread of the bore 16 in the distal part 10. The outer diameter D3' of the head 31 of the assembly screw 30 should be configured to fit with a loose fit to the diameter D3 of the enlarged section in the proximal part 20.

Figure 5A:
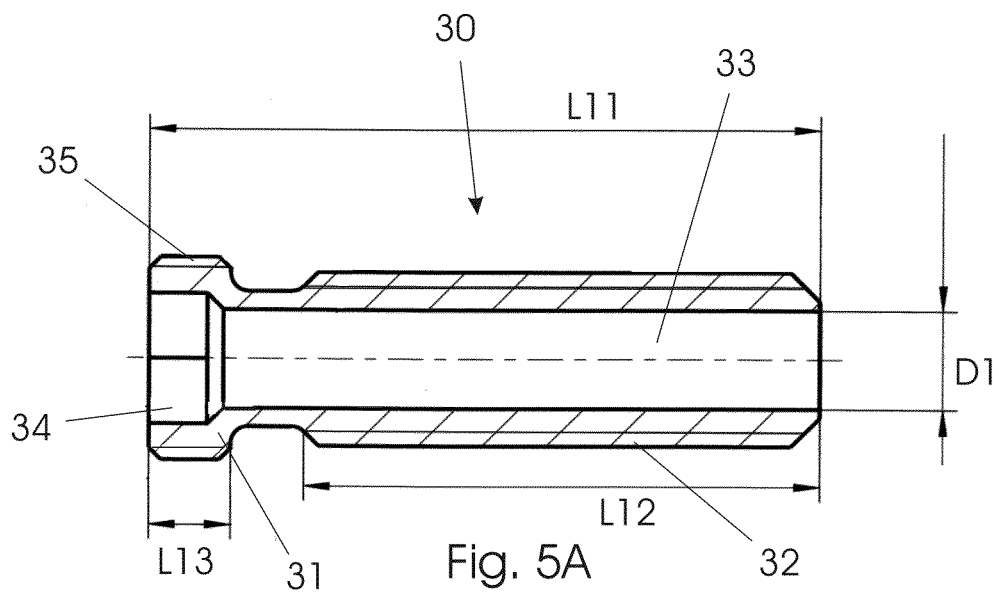
FIG. 5A is a sectional view and FIG. 5B is a side view of an assembly element according to a second embodiment.
Figure 5B:
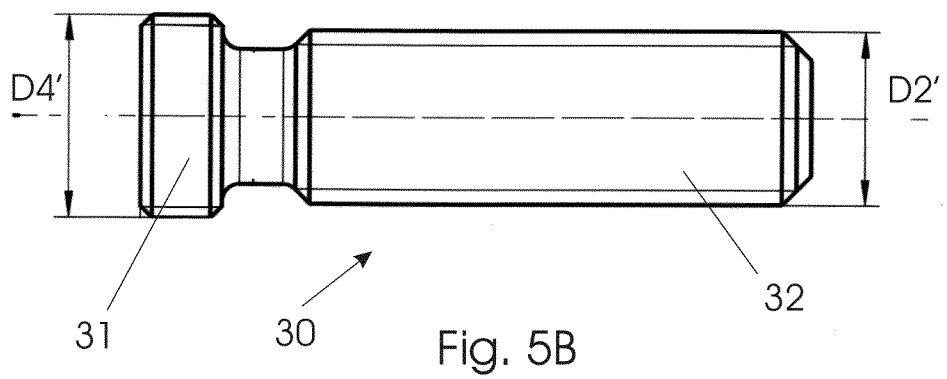

FIGS. 5A and 5B show a second embodiment of an assembly screw 30 with an outer thread 32 and a head 31. As the assembly screw 30 shown in FIGS. 4A and 4B, the assembly screw of FIGS. 5A and 5B comprises a through bore 33 as well as an inner tool engagement portion 34. Additionally, the second embodiment of the assembly screw 30 of FIGS. 5A and 5B comprises an additional outer thread 35 on the outer surface of the head 31. The additional outer thread 35 may be used as a blocking thread when the assembly screw 30 is inserted into the distal and proximal parts. The outer thread 35 may engage with an inner threaded portion 28 in the proximal part 20 as shown in FIG. 2B, so as to secure the assembly screw 30 within the distal and proximal parts.

In the following, examples of dimensions are provided for the dimensions denoted in the FIGS. with the respective reference signs.

The inner diameter D1 may be in the range between 3 mm and 4 mm, for example 3.4 mm.

The inner diameter D2, D2' may be in the range between 5 mm and 7.5 mm, for example a norm diameter of a metric thread M5, M6 or M7.

The inner diameter D3, D3' may be in the range between 6 mm and 9 mm, for example 8.1 mm.

The inner diameter D4, D4' may be in the range between 6 mm and 8 mm, for example a norm diameter of a metric thread M6 or M7.

The outer diameter D5 may be in the range between 9 mm and 11 mm, for example 10.5 mm.

The length L1 may be in the range between 5 mm and 9 mm, for example 6.5 mm.

The length L2 may be in the range between 4 mm and 8 mm, for example 5 mm.

The length L3 may be in the range between 6 mm and 11 mm, for example 8 mm.

The length L4 may be in the range between 15 mm and 20 mm, for example 17.5 mm.

The length L5 may be in the range between 10 mm and 14 mm, for example 12 mm.

The length L6 may be in the range between 2.5 mm and 3.5 mm, for example 3 mm.

The length L7 may be in the range between 10 mm and 30 mm, for example 15 mm or 23 mm.

The length L8 may be in the range between 8 mm and 14 mm, for example 11 mm.

The length L9 may be in the range between 3 mm and 20 mm, for example 4.5 mm or 17.7 mm.

The length L10 may be in the range between 2.5 mm and 3.5 mm, for example 3 mm.

The length L11 may be in the range between 2.5 mm and 5 mm, for example 2.8 mm or 4 mm.

Figure 6A:
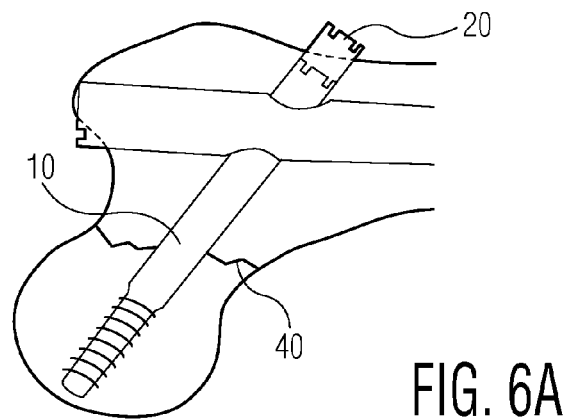
FIGS. 6A-C illustrate a migration of a lag screw.
Figure 6B:
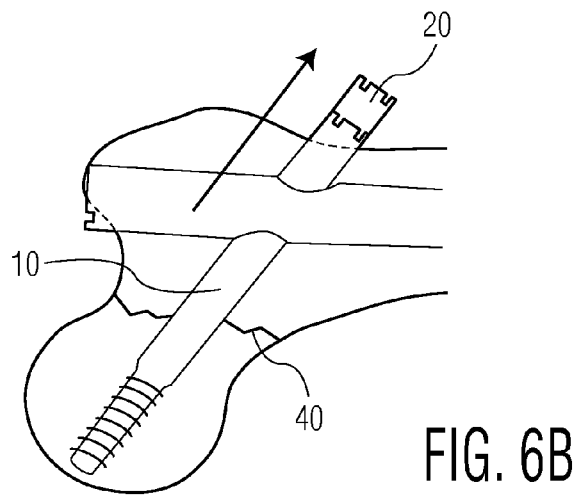
Figure 6C:
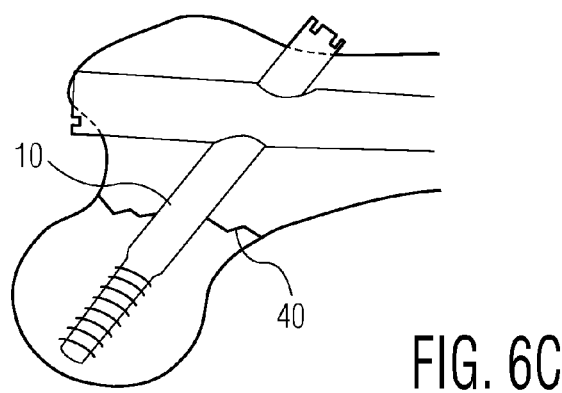

FIGS. 6A-C illustrate an application of a modular lag screw inserted through a bone nail and into a head of a femur. In FIG. 6A, a combination of a distal part 10 with an outer thread at its leading end portion and a proximal part 20 as a screw extension is inserted into a femur. Under load, it may occur that the bone at the fracture site 40 is compressed. As a result, the lag screw migrates in the direction of the arrow in FIG. 6B so that the trailing end of the modular lag screw protrudes out of the bone. Such a protrusion may cause irritation in the surrounding soft tissue. As depicted in FIG. 6C, the proximal part 20 of the modular lag screw may be removed. This may be done without removing the distal part 10 thus not effecting the stabilization of the femur neck at the fracture site 40.

Figure 7:
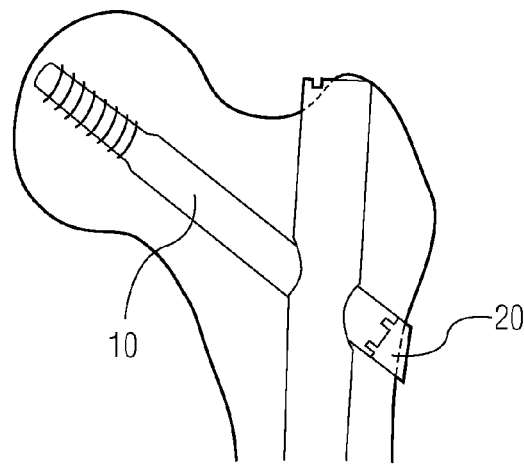
FIG. 7 shows a modular lag screw with a smooth end surface.

FIG. 7 shows an embodiment of a modular lag screw with a proximal part 20 having a smooth trailing end surface. The smooth end surface may be configured so as to form substantially the contour of the outer bone surface surrounding the trailing end of the lag screw when implanted, here the outer surface of the shaft portion of the femur at the location at which the lag screw has been introduced into the femur.

Figures 8A, 8B:
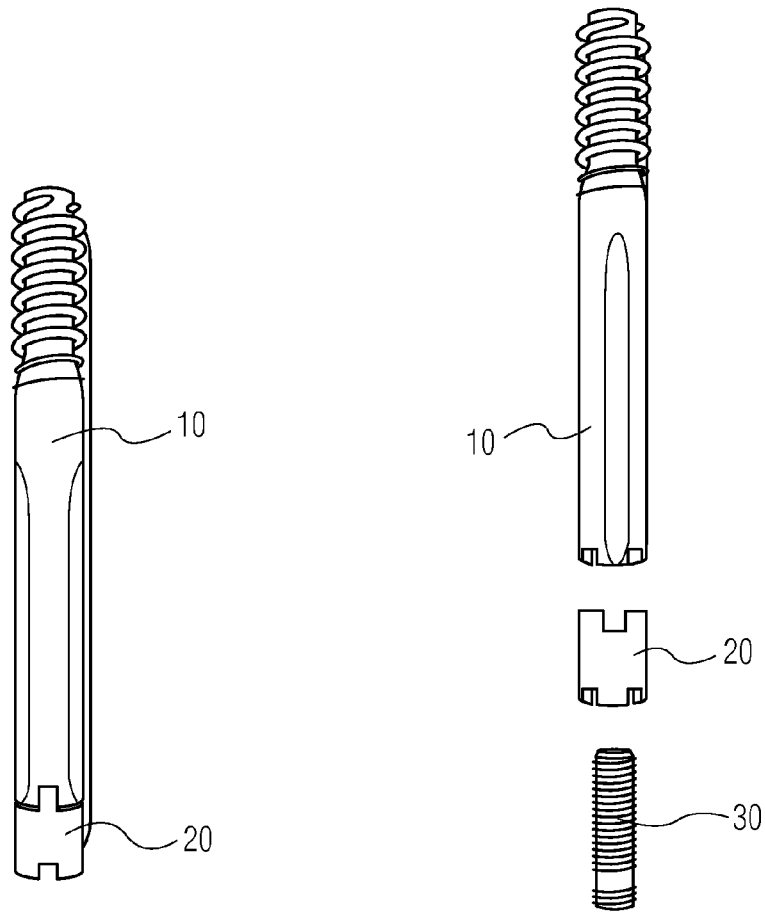
FIGS. 8A and 8B show an embodiment of a modular bone screw being assembled and disassembled, respectively, It is noted that the illustrations in the drawings are only schematically and not to scale. Throughout the drawings, the same reference numerals and characters, unless otherwise stated, are used to denote like features, elements, components, or portions of the illustrated embodiments. Moreover, while the present invention will now be described in detail with reference to the FIGS., it is done so in connection with the illustrative embodiments and is not limited by the particular embodiments illustrated in the FIGS., as defined by the appended claims.

FIG. 8A shows an embodiment of a modular bone screw with a distal part 10 and a proximal part 20 in an assembled condition. FIG. 8B shows an embodiment of a modular bone screw with a distal part 10 and a proximal part 20 in a disassembled condition. FIG. 8B further shows assembly element 30 which is adapted to be introduced through the proximal part 20 and into the distal part 10 to firmly couple the proximal part and the distal part.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone screw comprising:
   a distal part comprising a first leading end and a first trailing end, wherein the first trailing end includes a first tool engagement portion having at least one slot, and
   a proximal part comprising a second leading end and a second trailing end, wherein the second leading end includes a distal part engagement portion having at least one protrusion for an engagement with the at least one slot of the first tool engagement portion of the first trailing end of the distal part, and wherein the second trailing end includes a second tool engagement portion having a plurality of slots forming the second tool engagement portion, wherein the second tool engagement portion corresponds to the first tool engagement portion of the distal part, and
   an assembly element for firmly coupling the distal part and the proximal part when the first tool engagement portion of the distal part engages the distal part engagement portion of the proximal part.

2. The bone screw of claim 1, wherein the first tool engagement portion is crown-shaped.

3. The bone screw of claim 1, wherein the distal part engagement portion of the proximal part is formed so as to provide a form fit with the tool engagement portion of the distal part.

4. The bone screw of claim 1, wherein the distal part engagement portion at the second leading end of the proximal part is formed for an engagement with the tool engagement portion at the first trailing end of the distal part, and wherein the second trailing end of the proximal part comprises a second tool engagement portion which corresponds to the first tool engagement portion.

5. The bone screw of claim 1, wherein the proximal part comprises an end surface at the second trailing end section which corresponds to a shape of an outer bone surface at an intended implantation site so that the end surface of the bone screw is flush with the bone surface surrounding the end surface when the bone screw is inserted into the bone.

6. The bone screw of claim 5, wherein the end surface at the second trailing end section is inclined with respect to a longitudinal axis of the bone screw.

7. The bone screw of claim 1, wherein the distal part comprises an axial bore with an inner thread at the first trailing end, and the proximal part comprises an axial through bore with an enlarged section, wherein the assembly screw comprises a screw head being adapted to be received in the enlarged section in the proximal part and an outer screw thread being adapted to engage the inner thread in the distal part so as to firmly couple the distal part and the proximal part.

8. The bone screw of claim 1, wherein the distal part and the proximal part are configured to move over a guide wire when the first tool engagement portion of the distal part engages the distal part engagement portion of the proximal part.

9. The bone screw as set forth in claim 1 wherein the first engagement portion comprises a recess and the proximal part distal part engagement portion comprises a protrusion for engaging the recess, the proximal part having a bore therethrough.

10. The bone screw as set forth in claim 9 wherein the assembly element extends through the bore in the proximal part.

11. A bone screw comprising:
    a distal part comprising a first leading end and a first trailing end, wherein the first trailing end includes a first tool engagement portion with a plurality of slots, and
    a proximal part comprising a second leading end and a second trailing end, wherein the second leading end includes a distal part engagement portion with at least one protrusion for an engagement with the a plurality of slots of the first tool engagement portion of the first trailing end of the distal part, and wherein the second trailing end includes a second tool engagement portion with a plurality of slots, wherein the plurality of slots of the first tool engagement portion of the distal part is engagable with the plurality of slots of the second tool engagement portion of the proximal part, and
    an assembly element for firmly coupling the distal part and the proximal part when the first tool engagement portion of the distal part engages the distal part engagement portion of the proximal part, wherein the distal part comprises an axial bore with an inner thread at the first trailing end, and the proximal part comprises an axial through bore with an enlarged section, wherein the assembly screw comprises a screw head being adapted to be received in the enlarged section in the proximal part and an outer screw thread being adapted to engage the inner thread in the distal part so as to firmly couple the distal part and the proximal part.

12. The bone screw of claim 11, wherein the first tool engagement portion is crown-shaped.

13. The bone screw of claim 11, wherein the distal part engagement portion at the second leading end of the proximal part is formed for an engagement with the tool engagement portion at the first trailing end of the distal part, and wherein the second trailing end of the proximal part comprises a second tool engagement portion which corresponds to the first tool engagement portion.

14. The bone screw of claim 11, wherein the proximal part comprises an end surface at the second trailing end section which corresponds to a shape of an outer bone surface at an intended implantation site so that the end surface of the bone screw is flush with the bone surface surrounding the end surface when the bone screw is inserted into the bone.

15. The bone screw of claim 14, wherein the end surface at the second trailing end section is inclined with respect to a longitudinal axis of the bone screw.

16. The bone screw as set forth in claim 11 wherein the first engagement portion comprises a recess and the proximal part distal part engagement portion comprises a protrusion for engaging the recess, the proximal part having a bore therethrough.

17. A bone screw comprising:
    a distal part comprising a first leading end and a first trailing end, wherein the first trailing end includes a first tool engagement portion having at least one slot, and
    a proximal part comprising a second leading end and a second trailing end, wherein the second leading end includes a distal part engagement portion having at least one protrusion for an engagement with the at least one slot of the first tool engagement portion of the first trailing end of the distal part, and wherein the second trailing end includes a second tool engagement portion having a plurality of slots forming the second tool engagement portion, wherein the plurality of the slots of the second tool engagement portion of the proximal part corresponds to the first tool engagement portion, and an assembly element for firmly coupling the distal part and the proximal part when the first tool engagement portion of the distal part engages the distal part engagement portion of the proximal part.

18. The bone screw of claim 17, wherein the first tool engagement portion comprises at least one slot and the proximal portion distal part engagement portion comprises at least one protrusion for an engagement with the at least one slot.

19. The bone screw as set forth in claim 17 wherein the first engagement portion comprises a recess and the proximal part distal part engagement portion comprises a protrusion for engaging the recess, the proximal part having a bore therethrough.

* * * * *